United States Patent
Cline et al.

(10) Patent No.: US 10,610,228 B2
(45) Date of Patent: *Apr. 7, 2020

(54) PASSIVE NASAL PEEP DEVICES

(71) Applicant: Theravent, Inc., San Jose, CA (US)

(72) Inventors: Benjamin K. Cline, Vancouver (CA); Ronald G. French, Santa Clara, CA (US); Frank W. Wang, San Bruno, CA (US); Rajiv Doshi, Los Altos, CA (US); Ryan K. Pierce, Carl Junction, MO (US)

(73) Assignee: Theravent, Inc., San Jose, CA (US)

( * ) Notice: Subject to any disclaimer, the term of this patent is extended or adjusted under 35 U.S.C. 154(b) by 943 days.

This patent is subject to a terminal disclaimer.

(21) Appl. No.: 14/071,582

(22) Filed: Nov. 4, 2013

(65) Prior Publication Data

US 2014/0128761 A1    May 8, 2014
US 2016/0361067 A9    Dec. 15, 2016

Related U.S. Application Data

(63) Continuation-in-part of application No. 12/877,836, filed on Sep. 8, 2010, now Pat. No. 9,238,113, which
(Continued)

(51) Int. Cl.
*A61B 17/12* (2006.01)
*A61B 5/087* (2006.01)
(Continued)

(52) U.S. Cl.
CPC ...... *A61B 17/12104* (2013.01); *A61B 5/0871* (2013.01); *A61B 5/097* (2013.01);
(Continued)

(58) Field of Classification Search
CPC ............ A61M 16/208; A61M 16/0683; A61M 16/0666; A61M 16/08; A61M 2210/0618;
(Continued)

(56) References Cited

U.S. PATENT DOCUMENTS 69,396 A    10/1867 Curtis
628,111 A    7/1899 McHatton
(Continued)

FOREIGN PATENT DOCUMENTS

EP    0434258 A2    6/1991
EP    1157663 A1    11/2001
(Continued)

OTHER PUBLICATIONS

Doshi et al., U.S. Appl. No. 13/545,865 entitled "Nasal Devices," filed Jul. 10, 2012.
(Continued)

*Primary Examiner* — Samchuan C Yao
*Assistant Examiner* — Margaret M Luarca
(74) *Attorney, Agent, or Firm* — Shay Glenn LLP

(57) ABSTRACT

Described herein are passive nasal respiratory devices, in particular, passive nasal respiratory devices configured to achieve positive end-expiratory pressure (PEEP) in a subject wearing the device. PEEP devices may have a threshold pressure for opening during expiration. These devices may include a flap valve that opens on inhalation nested with a spring valve that opens when exhalation pressure exceeds a predetermined threshold. The device may be configured to be comfortably worn by a sleeping subject.

17 Claims, 12 Drawing Sheets

101 →

Related U.S. Application Data is a continuation of application No. 11/811,401, filed on Jun. 7, 2007, now Pat. No. 7,806,120, which is a continuation-in-part of application No. 11/298,640, filed on Dec. 8, 2005, now Pat. No. 7,735,492.

(60) Provisional application No. 61/721,928, filed on Nov. 2, 2012, provisional application No. 60/634,715, filed on Dec. 8, 2004, provisional application No. 60/811,814, filed on Jun. 7, 2006.

(51) Int. Cl.
    A61B 5/097     (2006.01)
    A61M 15/08    (2006.01)
    A61M 16/06    (2006.01)
    A61M 16/20    (2006.01)
    A61F 5/08     (2006.01)
    A61F 5/56     (2006.01)

(52) U.S. Cl.
    CPC ............ *A61F 5/08* (2013.01); *A61F 5/56* (2013.01); *A61M 15/08* (2013.01); *A61M 16/0666* (2013.01); *A61M 16/208* (2013.01); *A61M 16/06* (2013.01); *A61M 16/0683* (2013.01); *A61M 2210/0618* (2013.01)

(58) Field of Classification Search
    CPC .... A61M 15/08; A61M 16/20; A61M 16/207; A61F 5/56; A61B 5/097
    USPC ......................................... 128/207.13, 207.18
    See application file for complete search history.

(56) References Cited

U.S. PATENT DOCUMENTS

| | | |
|---|---|---|
| 669,098 A | 3/1901 | Overshiner |
| 675,275 A | 5/1901 | Gunning |
| 718,785 A | 1/1903 | McNary |
| 746,869 A | 12/1903 | Moulton |
| 774,446 A | 11/1904 | Moulton |
| 810,617 A | 1/1906 | Carence |
| 1,819,884 A | 8/1931 | Fores |
| 2,198,959 A | 4/1940 | Clarke |
| 2,237,954 A | 4/1941 | Wilson |
| 2,264,153 A | 11/1941 | Rowe |
| 2,274,886 A | 3/1942 | Carroll |
| 2,282,681 A | 5/1942 | Stotz |
| 2,335,936 A | 12/1943 | Hanlon |
| 2,433,565 A | 12/1947 | Korman |
| 2,448,724 A | 9/1948 | McGovney |
| 2,593,315 A | 4/1952 | Kraft |
| 2,672,138 A | 3/1954 | Oarlock |
| 2,751,906 A | 6/1956 | Irvine |
| 2,777,442 A | 1/1957 | Zelano |
| 3,145,711 A | 8/1964 | Beber |
| 3,315,701 A | 4/1967 | Stilwell |
| 3,370,305 A | 2/1968 | Goott et al. |
| 3,451,392 A | 6/1969 | Cook et al. |
| 3,463,149 A | 8/1969 | Albu |
| 3,513,839 A | 5/1970 | Vacante |
| 3,556,122 A | 1/1971 | Laerdal |
| 3,616,802 A | 11/1971 | Marinaccio |
| 3,657,855 A | 4/1972 | Swezey |
| 3,695,265 A | 10/1972 | Brevik |
| 3,710,799 A | 1/1973 | Caballero |
| 3,722,509 A | 3/1973 | Nebel |
| 3,747,597 A | 7/1973 | Olivera |
| 3,802,426 A | 4/1974 | Sakamoto |
| 3,884,223 A | 5/1975 | Keindl |
| 3,902,621 A | 9/1975 | Hidding |
| 4,004,584 A | 1/1977 | Geaney |
| 4,030,491 A | 6/1977 | Mattila |
| 4,040,428 A | 8/1977 | Clifford |
| 4,054,134 A | 10/1977 | Kritzer |
| 4,062,358 A | 12/1977 | Kritzer |
| 4,094,316 A | 6/1978 | Nathanson |
| 4,143,872 A | 3/1979 | Havstad et al. |
| 4,212,296 A | 7/1980 | Schaar |
| 4,220,150 A | 9/1980 | King |
| 4,221,217 A | 9/1980 | Amezcua |
| 4,226,233 A | 10/1980 | Kritzer |
| 4,240,420 A | 12/1980 | Riaboy |
| 4,267,831 A | 5/1981 | Aguilar |
| 4,325,366 A | 4/1982 | Tabor |
| 4,327,719 A | 5/1982 | Childers |
| RE31,040 E | 9/1982 | Possis |
| 4,354,489 A | 10/1982 | Riaboy |
| 4,403,616 A | 9/1983 | King |
| 4,456,016 A | 6/1984 | Nowacki et al. |
| 4,487,207 A | 12/1984 | Fitz |
| 4,533,137 A | 8/1985 | Sonne |
| 4,582,058 A | 4/1986 | Depel et al. |
| 4,584,997 A | 4/1986 | Delong |
| 4,601,465 A | 7/1986 | Roy |
| 4,640,277 A | 2/1987 | Meyer et al. |
| 4,651,873 A | 3/1987 | Stolcenberg et al. |
| 4,702,374 A | 10/1987 | Kelner |
| 4,718,554 A | 1/1988 | Barbato |
| 4,739,987 A | 4/1988 | Nicholson |
| 4,759,356 A | 7/1988 | Muir |
| 4,822,354 A | 4/1989 | Elosegui |
| 4,823,828 A * | 4/1989 | McGinnis ........... A61M 16/208 128/205.24 |
| 4,854,574 A * | 8/1989 | Larson ................. A63B 23/18 128/200.24 |
| 4,860,766 A | 8/1989 | Sackner |
| 4,862,903 A | 9/1989 | Campbell |
| 4,908,028 A | 3/1990 | Colon et al. |
| 4,913,138 A | 4/1990 | Yoshida et al. |
| 4,919,138 A | 4/1990 | Nordenstroom |
| 4,973,047 A | 11/1990 | Norell |
| 4,979,505 A | 12/1990 | Cox |
| 4,984,302 A * | 1/1991 | Lincoln ................. A62B 23/06 128/204.12 |
| 4,984,581 A | 1/1991 | Stice |
| 5,016,425 A | 5/1991 | Weick |
| 5,033,312 A | 7/1991 | Stupecky |
| 5,038,621 A | 8/1991 | Stupecky |
| 5,052,400 A | 10/1991 | Dietz |
| 5,059,208 A | 10/1991 | Coe et al. |
| 5,074,293 A | 12/1991 | Lott et al. |
| 5,078,739 A | 1/1992 | Martin |
| 5,092,781 A | 3/1992 | Casciotti et al. |
| 5,117,820 A | 6/1992 | Robitaille |
| 5,197,980 A | 3/1993 | Gorshkov et al. |
| 5,255,687 A | 10/1993 | McKenna |
| 5,383,470 A | 1/1995 | Kolbly |
| 5,385,542 A | 1/1995 | Rawlings |
| 5,391,205 A | 2/1995 | Knight |
| 5,392,773 A | 2/1995 | Bertrand |
| 5,394,867 A | 3/1995 | Swann |
| 5,414,627 A | 5/1995 | Wada et al. |
| 5,415,660 A | 5/1995 | Campbell et al. |
| 5,425,359 A | 6/1995 | Liou |
| 5,459,544 A | 10/1995 | Emura |
| 5,522,382 A | 6/1996 | Sullivan et al. |
| 5,535,739 A | 7/1996 | Rapoport et al. |
| 5,562,641 A | 10/1996 | Flomenblit et al. |
| 5,568,808 A | 10/1996 | Rimkus |
| 5,572,994 A | 11/1996 | Smith |
| 5,598,839 A | 2/1997 | Niles et al. |
| 5,607,469 A | 3/1997 | Frey |
| 5,649,533 A | 7/1997 | Oren |
| 5,665,104 A | 9/1997 | Lee |
| 5,727,546 A | 3/1998 | Clarke et al. |
| 5,730,122 A | 3/1998 | Lurie |
| 5,740,798 A | 4/1998 | McKinney |
| 5,743,256 A | 4/1998 | Jalowayski |
| 5,763,979 A | 6/1998 | Mukherjee et al. |
| 5,775,335 A | 7/1998 | Seal |
| 5,782,896 A | 7/1998 | Chen et al. |
| 5,797,920 A | 8/1998 | Kim |

(56) References Cited

U.S. PATENT DOCUMENTS

| | | | |
|---|---|---|---|
| 5,803,066 A * | 9/1998 | Rapoport | A61B 5/0002 128/204.21 |
| 5,803,121 A | 9/1998 | Estes | |
| 5,823,187 A | 10/1998 | Estes et al. | |
| 5,848,590 A | 12/1998 | Smith | |
| 5,865,170 A | 2/1999 | Moles | |
| 5,876,434 A | 3/1999 | Flomenblit et al. | |
| 5,878,743 A | 3/1999 | Zdrojkowski et al. | |
| 5,890,998 A | 4/1999 | Hougen | |
| 5,899,832 A | 5/1999 | Hougen | |
| 5,910,071 A | 6/1999 | Hougen | |
| 5,911,756 A | 6/1999 | Debry | |
| 5,947,119 A | 9/1999 | Reznick | |
| 5,954,766 A | 9/1999 | Zadno-Azizi et al. | |
| 5,957,978 A | 9/1999 | Blom | |
| 5,992,006 A | 11/1999 | Datsikas | |
| 6,004,342 A | 12/1999 | Filis | |
| 6,058,932 A | 5/2000 | Hughes | |
| 6,083,141 A | 7/2000 | Hougen | |
| D430,667 S | 9/2000 | Rome | |
| 6,119,690 A | 9/2000 | Pantaleo | |
| 6,165,133 A | 12/2000 | Rapoport et al. | |
| 6,176,234 B1 * | 1/2001 | Salter | A61M 15/00 128/200.14 |
| 6,177,482 B1 | 1/2001 | Cinelli et al. | |
| 6,189,532 B1 | 2/2001 | Hely et al. | |
| 6,213,955 B1 | 4/2001 | Karakasoglu et al. | |
| 6,219,997 B1 | 4/2001 | Friberg et al. | |
| 6,230,708 B1 * | 5/2001 | Radko | A61M 16/00 128/200.24 |
| 6,258,100 B1 | 7/2001 | Alferness et al. | |
| 6,287,290 B1 | 9/2001 | Perkins et al. | |
| 6,293,951 B1 | 9/2001 | Alferness et al. | |
| 6,311,839 B1 | 11/2001 | Lo | |
| 6,328,038 B1 | 12/2001 | Kessler et al. | |
| 6,369,126 B1 | 4/2002 | Cinelli et al. | |
| 6,398,775 B1 | 6/2002 | Perkins et al. | |
| 6,439,233 B1 | 8/2002 | Geertsema | |
| 6,484,725 B1 | 11/2002 | Chi | |
| 6,500,095 B1 | 12/2002 | Hougen | |
| 6,510,846 B1 * | 1/2003 | O'Rourke | A61M 15/0086 128/200.21 |
| 6,527,761 B1 | 3/2003 | Soltesz et al. | |
| 6,561,188 B1 | 5/2003 | Ellis | |
| 6,562,057 B2 | 5/2003 | Santin | |
| 6,568,387 B2 | 5/2003 | Davenport et al. | |
| 6,573,421 B1 | 6/2003 | Lemaire | |
| 6,581,598 B1 | 6/2003 | Foran et al. | |
| 6,585,639 B1 | 7/2003 | Kotmel et al. | |
| 6,592,594 B2 | 7/2003 | Rimbaugh et al. | |
| 6,592,995 B2 | 7/2003 | Topolkaraev et al. | |
| 6,595,215 B2 | 7/2003 | Wood | |
| 6,609,516 B2 | 8/2003 | Hollander et al. | |
| 6,626,172 B1 | 9/2003 | Karow et al. | |
| 6,626,179 B1 * | 9/2003 | Pedley | A61F 2/18 128/207.18 |
| 6,631,721 B1 | 10/2003 | Salter et al. | |
| 6,679,264 B1 | 1/2004 | Deem et al. | |
| 6,694,979 B2 | 2/2004 | Deem et al. | |
| 6,722,360 B2 | 4/2004 | Doshi | |
| 6,726,598 B1 | 4/2004 | Jarvis et al. | |
| 6,737,160 B1 | 5/2004 | Full et al. | |
| 6,769,432 B1 | 8/2004 | Keifer | |
| 6,776,162 B2 | 8/2004 | Wood | |
| 6,776,163 B2 | 8/2004 | Dougill et al. | |
| 6,811,538 B2 | 11/2004 | Westbrook et al. | |
| 6,841,716 B1 | 1/2005 | Tsutsumi | |
| 6,848,446 B2 | 2/2005 | Noble | |
| 6,863,066 B2 | 3/2005 | Ogle | |
| 6,866,652 B2 | 3/2005 | Bierman | |
| 6,872,439 B2 | 3/2005 | Fearing et al. | |
| 6,913,017 B2 | 7/2005 | Roberts | |
| 6,921,574 B2 | 7/2005 | Cinelli et al. | |
| 6,997,177 B2 | 2/2006 | Wood | |
| 7,011,723 B2 | 3/2006 | Full et al. | |
| 7,013,896 B2 | 3/2006 | Schmidt | |
| 7,047,969 B2 | 5/2006 | Noble | |
| 7,156,098 B2 | 1/2007 | Dolezal et al. | |
| 7,175,723 B2 | 2/2007 | Jones et al. | |
| 7,178,524 B2 | 2/2007 | Noble | |
| 7,201,169 B2 | 4/2007 | Wilkie et al. | |
| D542,407 S | 5/2007 | Stallard et al. | |
| 7,263,996 B2 | 9/2007 | Yung Ho | |
| 7,334,581 B2 | 2/2008 | Doshi | |
| D566,834 S | 4/2008 | Barton | |
| 7,422,014 B1 | 9/2008 | Smith | |
| 7,506,649 B2 | 3/2009 | Doshi et al. | |
| 7,559,326 B2 | 7/2009 | Smith et al. | |
| 7,578,294 B2 | 8/2009 | Pierro et al. | |
| 7,640,934 B2 | 1/2010 | Zollinger et al. | |
| 7,735,491 B2 | 6/2010 | Doshi et al. | |
| 7,735,492 B2 | 6/2010 | Doshi et al. | |
| 7,762,252 B2 | 7/2010 | Prete | |
| 7,798,148 B2 | 9/2010 | Doshi et al. | |
| 7,806,120 B2 | 10/2010 | Loomas et al. | |
| 7,856,979 B2 | 12/2010 | Doshi et al. | |
| 7,880,051 B2 | 2/2011 | Madsen et al. | |
| 7,987,852 B2 | 8/2011 | Doshi et al. | |
| 7,992,563 B2 | 8/2011 | Doshi | |
| 7,992,564 B2 | 8/2011 | Doshi et al. | |
| 7,992,566 B2 | 8/2011 | Pflueger et al. | |
| 8,020,700 B2 | 9/2011 | Doshi et al. | |
| 8,061,357 B2 | 11/2011 | Pierce et al. | |
| 8,215,308 B2 | 7/2012 | Doshi et al. | |
| 8,235,046 B2 | 8/2012 | Doshi et al. | |
| 8,240,309 B2 | 8/2012 | Doshi et al. | |
| 8,251,066 B1 | 8/2012 | Ho et al. | |
| 8,281,557 B2 | 10/2012 | Doshi et al. | |
| 8,291,909 B2 | 10/2012 | Doshi et al. | |
| 8,302,606 B2 | 11/2012 | Doshi et al. | |
| 8,302,607 B2 | 11/2012 | Pierce et al. | |
| 8,365,736 B2 | 2/2013 | Doshi et al. | |
| 8,707,955 B2 | 4/2014 | Doshi | |
| 2001/0051799 A1 | 12/2001 | Ingenito | |
| 2001/0056274 A1 | 12/2001 | Perkins et al. | |
| 2002/0062120 A1 | 5/2002 | Perkins et al. | |
| 2002/0077593 A1 | 6/2002 | Perkins et al. | |
| 2002/0112729 A1 | 8/2002 | DeVore et al. | |
| 2002/0157673 A1 | 10/2002 | Kessler et al. | |
| 2003/0024527 A1 | 2/2003 | Ginn | |
| 2003/0050648 A1 | 3/2003 | Alferness et al. | |
| 2003/0070682 A1 | 4/2003 | Wilson et al. | |
| 2003/0106555 A1 | 6/2003 | Tovey | |
| 2003/0106556 A1 | 6/2003 | Alperovich et al. | |
| 2003/0140925 A1 | 7/2003 | Sapienza et al. | |
| 2003/0149387 A1 | 8/2003 | Barakat et al. | |
| 2003/0154988 A1 | 8/2003 | DeVore et al. | |
| 2003/0158515 A1 | 8/2003 | Gonzalez et al. | |
| 2003/0195552 A1 | 10/2003 | Santin | |
| 2003/0209247 A1 | 11/2003 | O'Rourke | |
| 2004/0016432 A1 | 1/2004 | Genger et al. | |
| 2004/0020489 A1 | 2/2004 | Gillespie et al. | |
| 2004/0020492 A1 | 2/2004 | Dubrul et al. | |
| 2004/0020493 A1 | 2/2004 | Wood | |
| 2004/0055606 A1 | 3/2004 | Hendricksen et al. | |
| 2004/0112379 A1 | 6/2004 | Djupesland | |
| 2004/0123868 A1 | 7/2004 | Rutter | |
| 2004/0149615 A1 | 8/2004 | Eisenbraun | |
| 2004/0230108 A1 * | 11/2004 | Melker | A61B 5/0873 600/340 |
| 2004/0254491 A1 | 12/2004 | Ricciardelli | |
| 2004/0261791 A1 | 12/2004 | Horian | |
| 2004/0261798 A1 | 12/2004 | Rimkus | |
| 2005/0010125 A1 | 1/2005 | Joy et al. | |
| 2005/0011524 A1 | 1/2005 | Thomlinson et al. | |
| 2005/0033344 A1 | 2/2005 | Dillard et al. | |
| 2005/0051170 A1 | 3/2005 | Koo | |
| 2005/0066965 A1 | 3/2005 | Cronk et al. | |
| 2005/0076910 A1 | 4/2005 | Berthon-Jones et al. | |
| 2005/0133039 A1 | 6/2005 | Wood | |
| 2005/0211250 A1 | 9/2005 | Dolezal et al. | |
| 2005/0279351 A1 | 12/2005 | Lewis et al. | |
| 2005/0284479 A1 | 12/2005 | Schrader et al. | |

(56) References Cited

U.S. PATENT DOCUMENTS

| | | |
|---|---|---|
| 2006/0000472 A1 | 1/2006 | Fenton |
| 2006/0016450 A1 | 1/2006 | Pearson et al. |
| 2006/0085027 A1 | 4/2006 | Santin et al. |
| 2006/0169285 A1 | 8/2006 | Bovo |
| 2006/0180149 A1 | 8/2006 | Matarasso |
| 2006/0266361 A1 | 11/2006 | Hernandez |
| 2006/0278238 A1 | 12/2006 | Borody |
| 2006/0283461 A1 | 12/2006 | Lubke et al. |
| 2007/0016123 A1 | 1/2007 | Jensen |
| 2007/0051364 A1 | 3/2007 | Jacobson et al. |
| 2007/0095349 A1 | 5/2007 | Hansmann et al. |
| 2007/0175478 A1 | 8/2007 | Brunst |
| 2007/0227542 A1 | 10/2007 | Kashmakov et al. |
| 2007/0283962 A1 | 12/2007 | Doshi et al. |
| 2007/0287976 A1 | 12/2007 | Sherrill |
| 2007/0295338 A1* | 12/2007 | Loomas .............. A61M 15/08 128/207.18 |
| 2008/0023007 A1 | 1/2008 | Dolezal et al. |
| 2008/0032119 A1 | 2/2008 | Feldhahn et al. |
| 2008/0041397 A1 | 2/2008 | Hirs |
| 2008/0053460 A1 | 3/2008 | Wilson |
| 2008/0078383 A1 | 4/2008 | Richards et al. |
| 2008/0087286 A1 | 4/2008 | Jones |
| 2008/0099021 A1 | 5/2008 | Moore |
| 2008/0135044 A1 | 6/2008 | Freitag et al. |
| 2008/0142014 A1 | 6/2008 | Jiang |
| 2008/0142018 A1 | 6/2008 | Doshi et al. |
| 2008/0221470 A1 | 9/2008 | Sather et al. |
| 2009/0139530 A1 | 6/2009 | Landis et al. |
| 2009/0145441 A1 | 6/2009 | Doshi et al. |
| 2009/0194100 A1 | 8/2009 | Minagi |
| 2009/0194109 A1 | 8/2009 | Doshi et al. |
| 2009/0308398 A1 | 12/2009 | Ferdinand et al. |
| 2010/0326447 A1 | 12/2010 | Loomas et al. |
| 2011/0005520 A1 | 1/2011 | Doshi et al. |
| 2011/0067709 A1 | 3/2011 | Doshi et al. |
| 2011/0108041 A1 | 5/2011 | Sather et al. |
| 2011/0203598 A1 | 8/2011 | Favet et al. |
| 2011/0218451 A1 | 9/2011 | Lai et al. |
| 2011/0240038 A1 | 10/2011 | Doshi et al. |
| 2011/0290256 A1 | 12/2011 | Sather et al. |
| 2012/0285470 A9 | 11/2012 | Sather et al. |
| 2014/0109907 A1 | 4/2014 | Doshi et al. |
| 2014/0345623 A1 | 11/2014 | Pierce et al. |
| 2016/0128863 A1 | 5/2016 | Loomas et al. |
| 2018/0085246 A1 | 3/2018 | Loomas et al. |

FOREIGN PATENT DOCUMENTS

| | | |
|---|---|---|
| EP | 1205203 A2 | 5/2002 |
| EP | 1481702 A2 | 12/2004 |
| EP | 1917993 A1 | 5/2008 |
| FR | 2862614 A1 | 5/2005 |
| GB | 2096574 A | 10/1982 |
| GB | 2324729 A | 4/1998 |
| JP | 52-123786 A | 10/1977 |
| JP | 55-122742 U | 9/1980 |
| JP | 58-136345 A | 8/1983 |
| JP | 63-189257 U | 12/1988 |
| JP | 7-47126 | 2/1995 |
| JP | 3059270 U | 3/1999 |
| JP | 2001-299916 A | 10/2001 |
| JP | 2002-153489 A | 5/2002 |
| JP | 2002-219174 A | 8/2002 |
| JP | 2002-345963 A | 12/2002 |
| JP | 2002-345966 | 12/2002 |
| JP | 2005-40589 A | 2/2005 |
| JP | 2005-505355 | 2/2005 |
| JP | 2008-136496 | 6/2008 |
| JP | 2008-522763 | 7/2008 |
| RU | 2048820 C1 | 11/1995 |
| SU | 1586709 A1 | 8/1990 |
| WO | WO 90/12614 A1 | 11/1990 |
| WO | WO 93/08777 A1 | 5/1993 |
| WO | WO 95/17220 A1 | 6/1995 |
| WO | WO 95/33520 A1 | 12/1995 |
| WO | WO 98/46310 A2 | 10/1998 |
| WO | WO 99/03395 A1 | 1/1999 |
| WO | WO 00/29066 A1 | 5/2000 |
| WO | WO 00/50121 A1 | 8/2000 |
| WO | WO 00/67848 A1 | 11/2000 |
| WO | WO 01/02042 A1 | 1/2001 |
| WO | WO 01/13839 A1 | 3/2001 |
| WO | WO 01/13908 A2 | 3/2001 |
| WO | WO 01/49371 A2 | 7/2001 |
| WO | WO 01/87170 A1 | 11/2001 |
| WO | WO 01/89381 A1 | 11/2001 |
| WO | WO 02/38038 A2 | 5/2002 |
| WO | WO 03/022124 A2 | 3/2003 |
| WO | WO 03/034927 A1 | 5/2003 |
| WO | WO 2004/084998 A1 | 10/2004 |
| WO | WO 2005/000805 A2 | 1/2005 |
| WO | WO 2006/040585 A1 | 4/2006 |
| WO | WO 2007/023607 | 3/2007 |
| WO | WO 2007/129814 A1 | 11/2007 |
| WO | WO 2007/134458 A1 | 11/2007 |
| WO | WO 2007/146133 A2 | 12/2007 |

OTHER PUBLICATIONS

Witt et al.; U.S. Appl. No. 61/141,251 entitled "System, Method, and Respiration Appliance for Supporting the Airway of a Subject," filed Dec. 30, 2008.

http://chinookmed.com/index.cfm/fa/product.display&Product_ID=275; accessed Nov. 28, 2007.

Mahadevia, A. K. et al., Effects of expiratory positive airway pressure on sleep-induced respiratory abnormalities in patients with hypersomnia-sleep apnea syndrome, Am Rev Respir Dis 1983, vol. 128, pp. 708-711, Oct. 1983.

Dillard, D. et al., Evaluation of a novel intra-bronchial valve to produce lung volume reduction, World Congress of Bronchology, Jun. 2002 (figs. 1-4 available upon request).

Hakel et al.; Nasal obturator for velopharyngeal dysfunction in dysarthria: technical report on a one-way valve; Journal of Medical Speech-Language Pathology; vol. 12; No. 4; pp. 155-159; Dec. 2004.

Suwaki et al.; Nasal speaking valve: a device for managing velopharyngeal incompetence; Journal of Oral Rehabilitation; vol. 35(1); pp. 73-78; Jan. 2008.

Suwaki et al.; The effect of nasal speaking valve on the speech under experimental velopharyngeal incompetence condition; Journal of Oral Rehabilitation; vol. 35(5); pp. 361-369; May 2008.

\* cited by examiner

PASSIVE NASAL PEEP DEVICES

CROSS REFERENCE TO RELATED APPLICATIONS

This patent application claims priority to U.S. Provisional Patent Application No. 61/721,928, filed on Nov. 2, 2012, and titled "PASSIVE NASAL PEEP DEVICES," which is herein incorporated by reference in its entirety.

This patent application also claims priority as a continuation-in-part to U.S. patent application Ser. No. 12/877,836, filed on Sep. 8, 2010 (now U.S. Pat. No. 9,238,113), and titled "NASAL RESPIRATORY DEVICES FOR POSITIVE END-EXPIRATORY PRESSURE," which is a continuation of U.S. patent application Ser. No. 11/811,401, filed on Jun. 7, 2007, titled "NASAL RESPIRATORY DEVICES FOR POSITIVE END-EXPIRATORY PRESSURE" (now U.S. Pat. No. 7,806,120), which is a continuation-in-part of U.S. patent application Ser. No. 11/298,640, filed on Dec. 8, 2005, titled "NASAL RESPIRATORY DEVICES" (now U.S. Pat. No. 7,735,492), which claims priority to U.S. Provisional Patent Application No. 60/634,715, filed on Dec. 8, 2004, which are herein incorporated by reference. U.S. patent application Ser. No. 11/811,401 also claims priority to U.S. Provisional Patent Application No. 60/811,814, filed on Jun. 7, 2006, titled "RESPIRATORY DEVICES." Each of the above patents and patent applications are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The devices and methods described herein relate to passive nasal devices that provide positive end-expiratory pressure (PEEP) when secured in contact with the wearer's nose or nasal passages. These devices are lightweight, easy to apply, effective, and may be safely worn while sleeping.

BACKGROUND

Positive end-expiratory pressure (PEEP) refers to pressure in the airway at the end of expiration that exceeds atmospheric pressure. Positive end-expiratory pressure has been used clinically mainly as a way to recruit or stabilize lung units and improve oxygenation in patients with hypoxemic respiratory failure. Traditionally, PEEP has been achieved using devices that apply continuous positive airway pressure (referred to as ventilators or CPAP devices), wherein both the inspiratory and expiratory portions of the circuit are pressurized above atmospheric pressure. However, CPAP devices (including modified devices such as "C-FLEX" devices manufactured by Respironics) are expensive, uncomfortable and cumbersome, leading to limited application and patient compliance.

Numerous disease states may benefit from the modification of patient respiration to induce PEEP, including heart failure, sleep apnea and other sleep disorders, hypertension, snoring, chronic obstructive pulmonary disease (COPD), bronchitis, asthma, and many others.

Heart failure, or congestive heart failure (CHF), is a common clinical syndrome that represents the end-stage of a number of pulmonary and cardiac disease states. Heart failure is a degenerative condition that occurs when the heart muscle weakens and the ventricle no longer contracts normally. The heart can then no longer adequately pump blood to the body including the lungs. This may lead to exercise intolerance, or may cause fluid retention with subsequent shortness of breath or swelling of the feet. Over four million people are diagnosed with heart failure in the United States alone. Morbidity and mortality in patients with heart failure is high.

Sleep apnea is defined as the temporary absence or cessation of breathing during sleep. Airflow must be absent for some period of time longer than the usual inter-breath interval, typically defined as ten seconds for adults and eight seconds (or more than two times the normal respiratory cycle time) for infants. There are different varieties of sleep apnea, including central, obstructive, complex, and mixed. In central sleep apnea, the patient makes no effort to breathe. In obstructive apnea, ventilatory effort is present, but no airflow results, because of upper airway closure. In mixed apnea, there is initially no ventilatory effort (suggestive of central sleep apnea), but an obstructive sleep apnea pattern becomes evident when ventilatory effort resumes. Finally, hypopnea is a temporary decrease in inspiratory airflow relative to the previous several inspirations. The terms sleep apnea and/or sleep disordered breathing may refer to hypopnea.

Hypertension refers to elevated blood pressure, and is a very common disease. Hypertension is characterized by elevated systolic and/or diastolic blood pressures. Despite the prevalence of hypertension and its associated complications, control of the disease is far from adequate. Only a third of people with hypertension control their blood pressure adequately. This failure reflects the inherent problem of maintaining long-term therapy for a usually asymptomatic condition, particularly when the therapy may interfere with the patient's quality of life, and when the immediate benefits of the therapy are not obvious to the patient.

Chronic obstructive pulmonary disease (COPD) includes chronic bronchitis, emphysema and asthma. In both chronic bronchitis and emphysema, airflow obstruction limits the patient's airflow during exhalation. COPD is a progressive disease characterized by a worsening baseline respiratory status over a period of many years with sporadic exacerbations often requiring hospitalization. Early symptoms include increased sputum production and sporadic acute exacerbations characterized by increased cough, purulent sputum, wheezing, dyspnea, and fever. As the disease progresses, the acute exacerbations become more frequent. Late in the course of the disease, the patient may develop hypercapnia, hypoxemia, erythrocytosis, cor pulmonale with right-sided heart failure, and edema.

Chronic bronchitis is characterized by a chronic cough with sputum production leading to obstructed expiration. Pathologically, there may be mucosal and submucosal edema and inflammation and an increase in the number and size of mucus glands. Emphysema is characterized by destruction of the lung parenchyma leading to loss of elastic recoil, reduced tethering of airways, and obstruction to expiration. Pathologically, the distal airspaces are enlarged.

Asthma is another chronic lung condition, characterized by difficulty in breathing. People with asthma have extra-sensitive or hyper-responsive airways. The airways react by obstructing or narrowing when they become inflamed or irritated. This makes it difficult for the air to move in and out of the airways, leading to respiratory distress. This narrowing or obstruction can lead to coughing, wheezing, shortness of breath, and/or chest tightness. In some cases, asthma may be life threatening.

In all of these diseases, current medical and surgical therapies are not completely effective, and there is considerable room for improvement. Two therapies that are used to treat these diseases are pulmonary rehabilitation (including pursed-lip breathing) and non-invasive mechanical ventilation.

Pulmonary rehabilitation is frequently used to treat patients suffering from a variety of medical ailments such as those mentioned. For example, COPD patients are taught new breathing techniques that reduce hyperinflation of the lungs and relieve expiratory airflow obstruction. One of the goals of this training is to reduce the level of dyspnea. Typically, these new breathing techniques include diaphragmatic and pursed-lip breathing. Pursed-lip breathing involves inhaling slowly through the nose and exhaling through pursed-lips (as if one were whistling), taking two or three times as long to exhale as to inhale. Most COPD patients instinctively learn how to perform pursed-lip breathing in order to relieve their dyspnea. Moreover, patients with asthma and other respiratory ailments, and even normal people during exercise, have been shown to use pursed-lip breathing, especially during times of exertion.

It is widely believed that producing a proximal obstruction (e.g., pursing the lips) splints open the distal airways that have lost their tethering in certain disease states. In other words, airways that would normally collapse during respiration remain open when the patient breathes through pursed-lips. Moreover, by increasing exhalation time, respiratory rate can be reduced and, in some cases, made more regular.

The medical literature has confirmed the utility of pursed-lip breathing in COPD patients. Specifically, it has been found that pursed-lip breathing by COPD patients results in a reduction in respiratory rate, an increase in tidal volumes, and an improvement of oxygen saturation. All of these effects contribute to a reduction in patient dyspnea. However, pursed-lip breathing requires conscious effort. Thus, the patient cannot breathe through pursed-lips while sleeping. As a result, the patient can still become hypoxic at night and may develop pulmonary hypertension and other sequelae as a result. Furthermore, the patient has to constantly regulate his own breathing. This interferes with his performing of other activities because the patient must pay attention to maintaining pursed-lip breathing.

Non-invasive positive pressure ventilation (NPPV) is another method of treating diseases that benefit from regulation of the patient's respiration. NPPV refers to ventilation delivered by a nasal mask, nasal prongs/pillows or face mask. NPPV eliminates the need for intubation or tracheostomy. Outpatient methods of delivering NPPV include bilevel positive airway pressure (BIPAP or bilevel) ventilator devices, or continuous positive airway pressure (CPAP) devices.

NPPV can deliver a set pressure during each respiratory cycle, with the possibility of additional inspiratory pressure support in the case of bi-level devices. NPPV has been shown to be very efficacious in such diseases as sleep apnea, heart failure, and COPD, and has become increasingly used in recent years. Many patients use CPAP or BIPAP at night while they are sleeping.

However, most patients experience difficulty adapting to nocturnal NPPV, leading to poor compliance. Mask discomfort is a very common problem for patients new to NPPV, because of the high pressures on the nose, mouth, and face, and because of uncomfortably tight straps. Nasal congestion and dryness are also common complaints that may vary by season. The nasal bridge can become red or ulcerated due to excessive mask tension. Eye irritation and acne can also result. Still other patients experience abdominal distention and flatulence. Finally, air leakage through the mouth is also very common in nasal NPPV patients, potentially leading to sleep arousals.

Both pursed-lip breathing and the use of NPPV have been shown to offer significant clinical benefits to patients with a variety of medical illnesses, including but not limited to COPD, heart failure, pulmonary edema, sleep apnea (both central and obstructive) and other sleep disordered breathing, cystic fibrosis, asthma, cardiac valve disease, arrhythmias, anxiety, and snoring. Expiratory resistance is believed to provide the bulk of clinical improvements when using pursed-lip breathing and NPPV, through a variety of physiologic mechanisms. In contrast, inspiratory support is not believed to offer clinical benefits in many patients. For example, in COPD, expiratory resistance facilitates expiration, increases tidal volume, decreases respiratory rate, and improves gas exchange. In the case of heart failure, it is felt that positive pressure in the airways (due to expiratory resistance) reduces pulmonary edema and improves lung compliance, decreases preload and afterload, increases $pO_2$, and decreases $pCO_2$. In many disease states, expiratory resistance helps maintain a more stable respiratory rate that can have profound clinical effects to the patient.

It would therefore be desirable to have a medical device and/or procedure that mimics the effect of pursed-lip breathing and/or the benefits of non-invasive ventilation without suffering from the drawbacks described above.

SUMMARY OF THE DISCLOSURE

Described herein are nasal respiratory devices and methods for treating a variety of medical diseases through the use of such devices. For example, described herein are nasal respiratory devices for inducing positive end-expiratory pressure adapted to be secured, e.g., removably, and in some cases adhesively, secured, in communication with a nasal cavity. These devices may include an opening or passageway, and an airflow resistor in communication with the opening/passageway, wherein the airflow resistor is configured to have a non-zero threshold pressure for opening during expiration so that the airflow resistor is closed during expiration when the pressure across the airflow resistor is below the threshold pressure for opening, but the airflow resistor opens during expiration when the airflow resistor exceeds the threshold pressure for opening during expiration. These devices may also include a holdfast configured to secure the airflow resistor in communication with the nasal cavity without covering the subject's mouth.

Although the airflow resistors described herein may be referred to as closed during expiration at pressures below the threshold, it should be understood that there may be some airflow, even at low pressures, by design, in some variations. Thus, closure of the airflow resistor typically means that the valve of the airflow resistor is in a closed position, though some air may pass through the device, including the airflow resistor (non-zero flow).

The devices described herein may be adhesive, and may be configured to secure over, across and/or slightly within one or both of a subject's nostrils. These devices may include an adhesive holdfast that extends roughly perpendicular to a body (e.g., valve body, cone) housing a dual airflow resistor (valve) that includes an inspiratory valve component and an expiratory valve component. For example, the inspiratory valve component may be a flap-valve that opens during inhalation through the device, and the expiratory valve component may be a piston-type valve including a bias preventing the valve from opening until the expiratory pressure exceeds a threshold. In some variations the inspiratory valve is nested in the expiratory valve.

The variations described herein are particularly well suited for use as nasal respiratory valves, and especially valves that may be used by a sleeping or recumbent patient. For example, the valves described herein may be adapted to be worn comfortably on the patient's face. Such adaptations include the use of the holdfast configurations described herein, the overall low profile of the devices, and the shape of the device, including the body (cone) region.

Any appropriate threshold pressure for opening during expiration may be used. For example, the threshold pressure for opening (which may also be referred to as the threshold for opening) of the airflow resistor may be less than about 20 cm $H_2O$, less than about 15 cm $H_2O$, less than about 13 cm $H_2O$, less than about 10 cm $H_2O$, less than about 8 cm $H_2O$, more than about 4 cm $H_2O$, or between a range of pressures. For example, the threshold pressure for opening may be between about 0.5 cm $H_2O$ and about 20 cm $H_2O$, or between about 0.5 cm $H_2O$ and about 15 cm $H_2O$, or between about 4 cm $H_2O$ and about 20 cm $H_2O$. The threshold for opening is typically much less than the pressure resulting from coughing, sneezing, or the like.

In some variations, the airflow resistor may further comprise a non-zero threshold pressure for closing during expiration, such that the airflow resistor closes during expiration when the pressure across the airflow resistor falls below the threshold pressure for closing. Any appropriate threshold pressure for closing during expiration may be used. For example, the threshold pressure for closing during expiration may be greater than about 1 cm $H_2O$, greater than about 2 cm $H_2O$, greater than about 3 cm $H_2O$, greater than about 4 cm $H_2O$, greater than about 10 cm $H_2O$, etc. In some variations, the threshold pressure for closing during expiration is between a range of values, such as between about 0.5 cm $H_2O$ and about 20 cm $H_2O$, between about 0.5 cm $H_2O$ and about 15 cm $H_2O$, between about 0.5 cm $H_2O$ and about 10 cm $H_2O$, between about 0.5 cm $H_2O$ and about 5 cm $H_2O$. The threshold pressure for closing during expiration may be approximately the same as the threshold pressure for opening during expiration, or it may be different.

The passive nasal respiratory devices for inducing positive end-expiratory pressure described herein may be adapted to be secured in communication with a nasal cavity so that the body of the device (housing at least one of the expiratory and/or inspiratory valves forming the airflow resistor) is communication with one or more nasal passage, so that the airflow resistor is closed during expiration when the pressure across the valve is below the threshold pressure for opening, but the valve opens during expiration when the pressure across the valve exceeds the threshold pressure for opening during expiration. These devices may also include a holdfast configured to secure the airflow resistor only in communication with a nasal cavity, or with both nasal cavities (e.g., but not the mouth). The airflow resistor may include a flap valve and a biased valve configured as a nested valve, a bistable valve, and the like.

Also described herein are passive nasal respiratory devices for inducing positive end-expiratory pressure adapted to be secured in communication with a nasal cavity that include a passageway through a housing and an airflow resistor in communication with the housing, where the airflow resistor has a first valve configured to open during inspiration and close during expiration and a second valve configured to open during exhalation and close during inspiration, and the second valve is configured so that it does not open until the pressure across the second valve exceeds a non-zero threshold pressure for opening. These devices may also include a holdfast extending from the body of the device in a direction roughly perpendicular to the direction of air through the housing. The holdfast may be an adhesive holdfast configured to secure the airflow resistor in communication with the nasal cavity.

A passive nasal device (or passive airflow resistor) typically does not include active elements (e.g., powered elements) or driven airflow, as from pressurized gas, fans, or the like. Thus, a passive airflow resistor may be configured to provide resistance based on the mechanical operation of the airflow resistor during inhalation and exhalation through the device.

In some variations, the second valve is nested with the first valve. The first valve or the second valve (or both) may be a flap valve. The second valve may be a biased valve (including but not limited to a biased flap valve). The second valve may be a bistable valve.

These passive nasal respiratory devices for inducing positive end-expiratory pressure may be adapted to be secured in communication with one or both nasal cavities.

Any of the passive nasal PEEP devices described herein may be used to treat a disorder. Methods of treating a disorder with these devices may include the steps of securing one or the devices described herein in communication with a subject's nasal cavity without covering the subject's mouth, wherein the respiratory device comprises an airflow resistor configured to have a non-zero threshold pressure for opening during expiration so that the airflow resistor is closed during expiration when the pressure across the valve is below the threshold pressure for opening, but the airflow resistor opens during expiration when the pressure across the airflow resistor exceeds the threshold pressure for opening during expiration, and allowing the subject to breathe at least partly through the nasal respiratory device. The disorder treated may be selected from the group consisting of: respiratory disorders, sleep disorders, gastroenterologic disorders, and cardiovascular disorders.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The passive nasal PEEP devices described herein may be used to create positive end expiratory pressure during respiration (PEEP) effect in a subject wearing the device are described. These respiratory devices are referred to as passive nasal PEEP devices or simply as "devices." The devices and methods described herein may be useful to treat a variety of medical disease states, and may also be useful for non-therapeutic purposes. The devices and methods described herein are not limited to the particular embodiments described. It is also to be understood that the examples and particular embodiments described are not intended to be limiting.

As used in this specification, the singular forms "a," "an," and "the" include plural reference unless the context clearly dictates otherwise. Unless defined otherwise, all technical and scientific terms used herein have the same meaning as commonly understood by one of ordinary skill in the art.

As used herein a passive nasal device is one that does not require the addition of a pressurized source of respiratory gas to operate as described (e.g., to apply PEEP and limit exhalation more than inhalation).

Figure 1A:
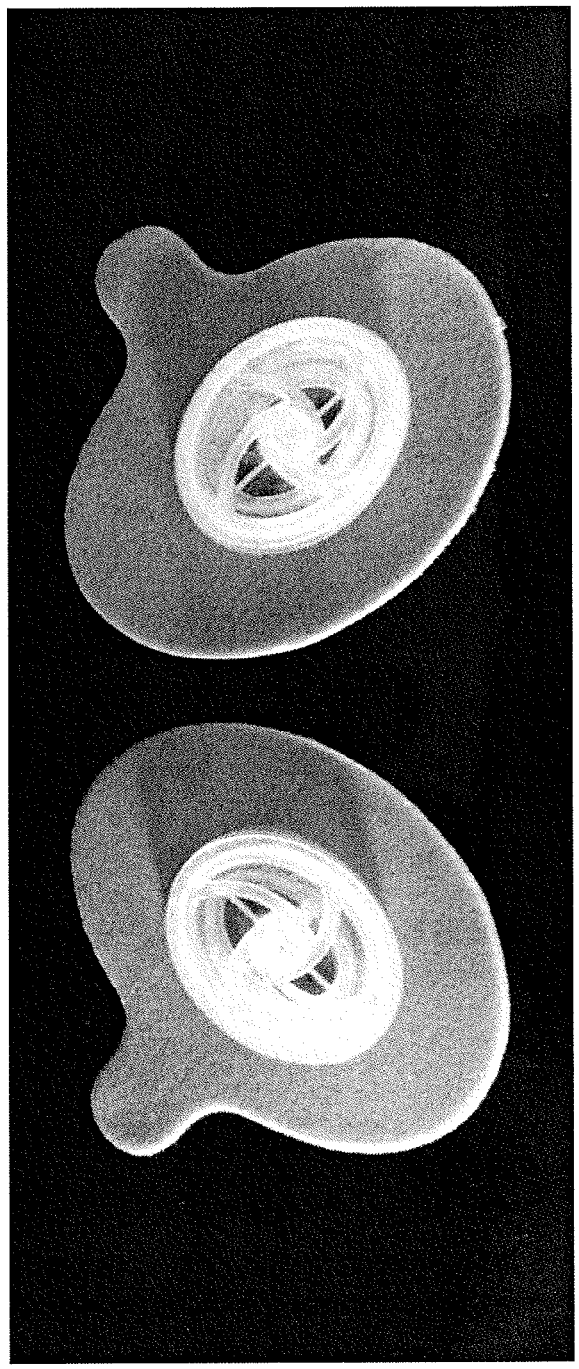
FIGS. 1A and 1B shows one variations of a pair of passive nasal PEEP devices from a top and side perspective view, respectively. The device maintains substantially constant pressure throughout range of expiratory flow, while remaining comfortable. The device used by a particular patient may be chosen to correspond to a patient's titrated CPAP level, as discussed below.
Figure 1B:
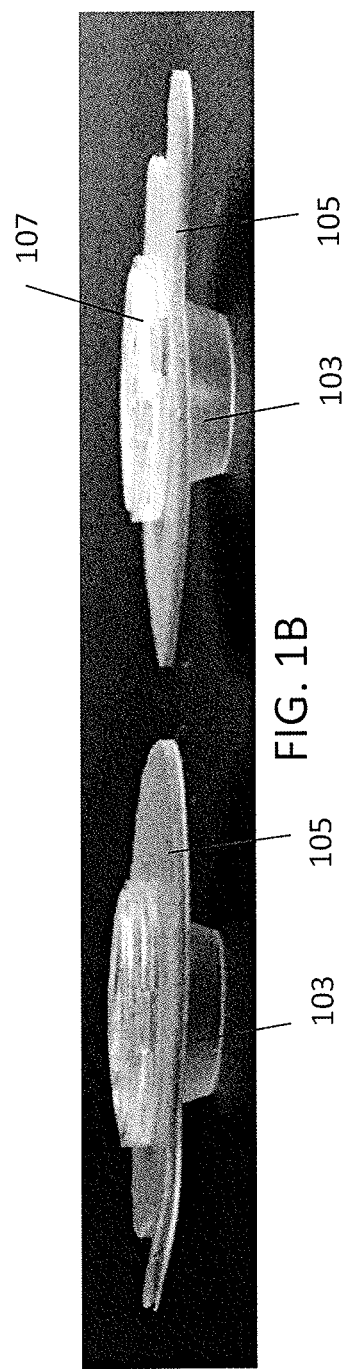
Figure 2:
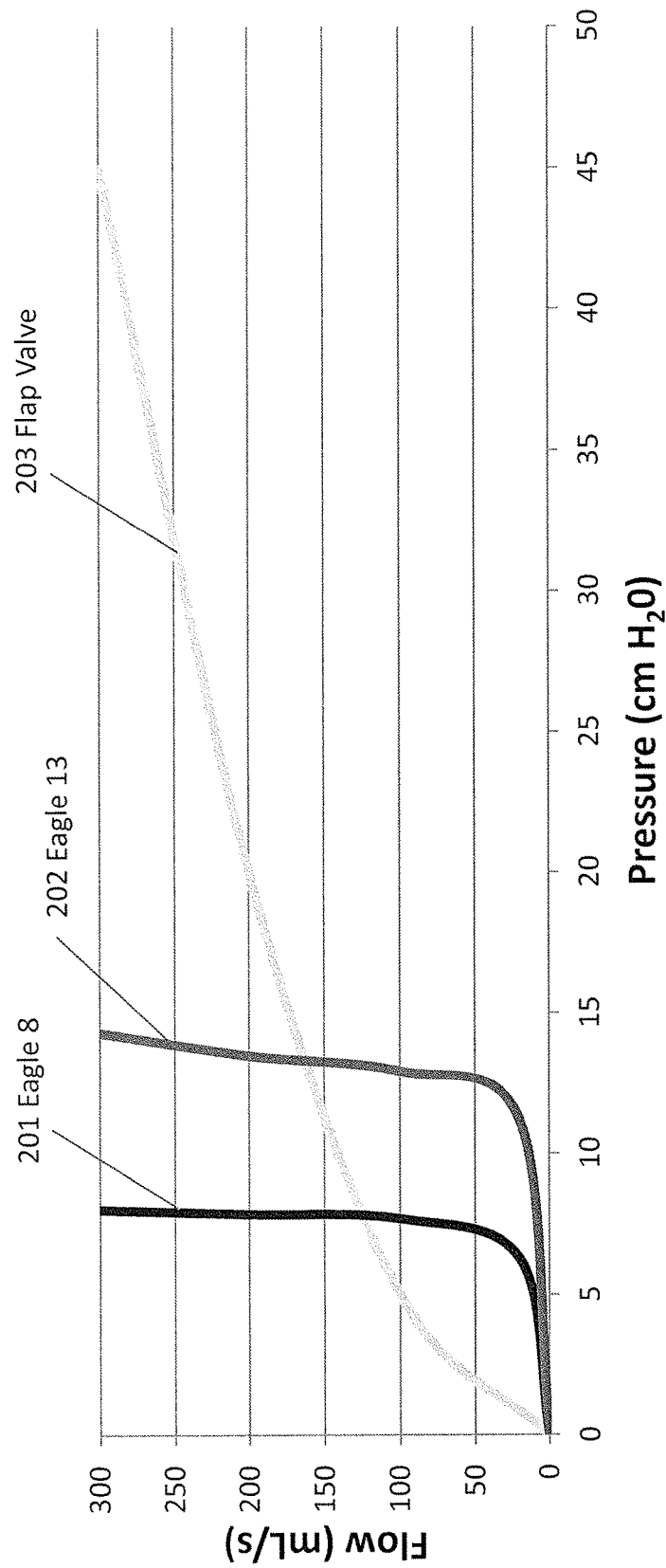
FIG. 2 is a graph illustrating the pressure/flow profile for a variation of a passive nasal PEEP device similar to that shown in FIGS. 1A and 1B.

FIGS. 1A and 1B illustrate one variation of a pair of passive nasal PEEP devices 101 that may be placed over (and slightly into) a subject's nostrils in order to inhibit exhalation more than inhalation and create PEEP within the subject. The device shown in FIGS. 1A and 1B includes an adhesive holdfast 105, a cone or body region 105 that is capped with the outer cap 107 (having a spiral pattern) that prevents the valves (both the inhalation flap valve that is nested within the exhalation spring or post valve) from leaving the cone or body region. The holdfast extends from body in a direction that is perpendicular to the path air takes through the body. As is apparent in FIG. 1B, the body region 103 or cone extends past the holdfast, and may extend into the nostril(s) of the wearer. The overall thickness of the body region is limited to less than a cm (e.g., less than 0.8 cm, less than 0.7 cm, less than 0.6 cm, less than 0.5 cm, etc.), but the thickness is sufficient for the expiratory valve of the airflow resistor to be displaced if the expiratory pressure exceeds the threshold value, and for the inspiratory valve to open during inhalation without interference (e.g., from nose hairs, nasal tissue, etc.). FIG. 2 illustrates the resistance through exemplary devices as described herein during exhalation. The first line 203 ("Flap Valve") shows a device that is not configured as a PEEP valve having a single passive nasal airflow resistor (in this example, having flap valves). The device opens immediately, and the flow increases with pressure towards a linear slope (with flow increasing as pressure increases). In contrast the "Eagle 8" 201 and "Eagle 13" 202 devices are passive nasal PEEP devices that have opening thresholds of 8 and 13 cm $H_2O$, respectively. As pressure increases in these devices, flow is zero until the threshold, then flow increases dramatically (exponentially) as pressure increases.

Figure 10:
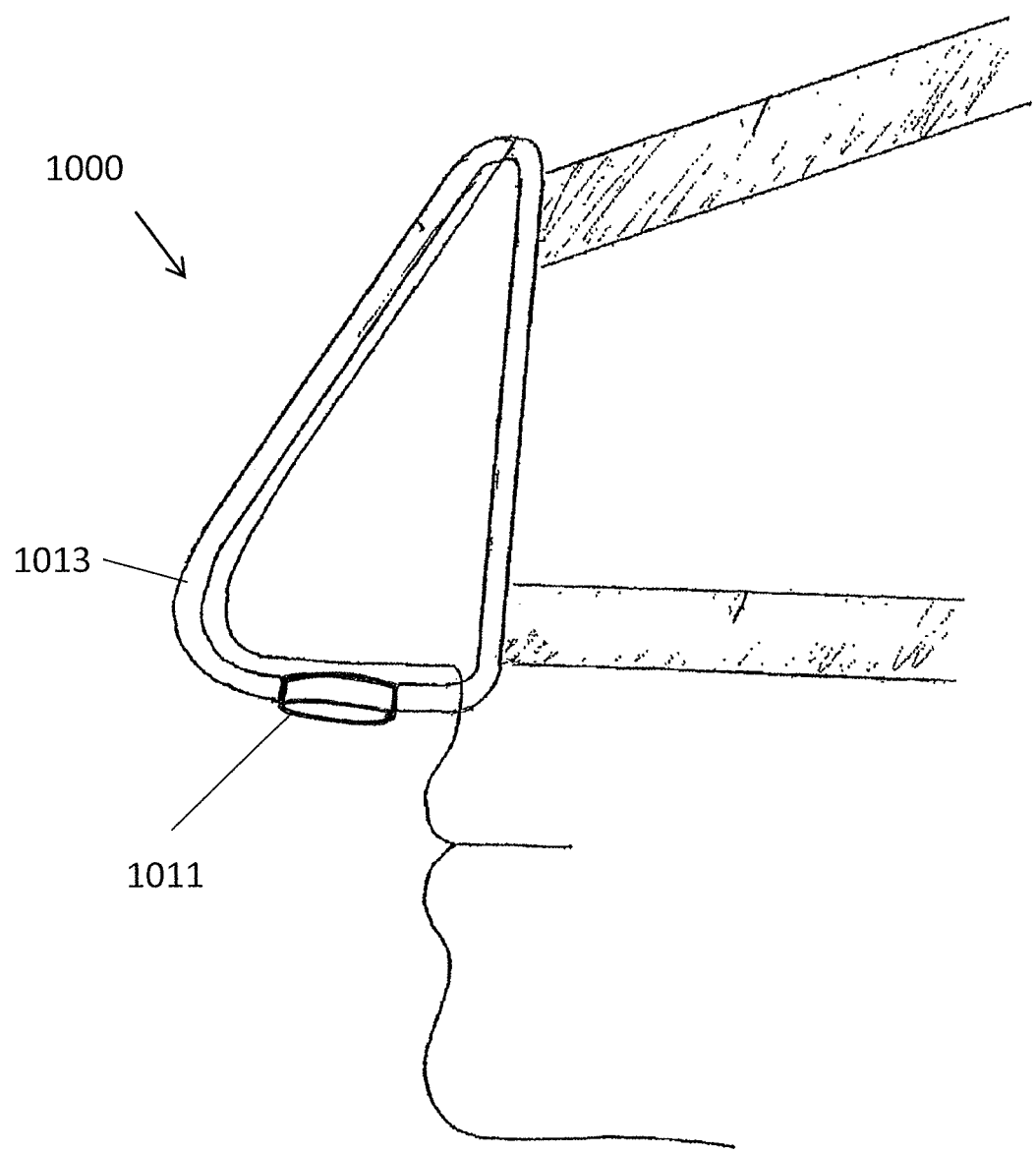
FIG. 10 illustrates a variation of a device included on (or in some variations integral with) a nasal mask.

Any of the valves described herein can also be placed on a mask that fits on the nose or on a mask that fits on the nose and mouth. Such a mask may be held onto the head by adhesive or alternatively with straps or the like. Such a mask may be reusable or disposable by the patient. For example, FIG. 10 illustrates a mask-type nasal device 1000 including a passive nasal PEEP airflow resistor 1011 as described herein. In some variations the valve 1011 is integral to the mask 1012. In some variations the valve includes an adhesive holdfast that could be applied directly to a subject's nose, but is instead secured over a reusable nasal mask having one or more opening(s) to position the nasal device over the subject's nostril(s).

FIGS. 3 through 8B illustrate various component parts of a nasal PEEP device such as the one shown in FIG. 1A. Any of the devices described herein may include some or all of these component parts. FIGS. 3 to 8B illustrate the cap region, piston, and body which form the PEEP-type (a passive PEEP valve) that can be adhesively secured to the nose. The PEEP valve may include a spring (not visible in the figures) that can couple to the post and provide the preloaded resistance that is overcome by expiratory resistance above a predetermined level; above this threshold, the cap allows the passage expiratory airflow by displacing all or a portion of the cap. An internal flap valve may be included and arranged so that it can be opened by inhalation (allow easy inhalation) but closed during exhalation; above a threshold expiratory pressure the flap valve may remain closed while the cap or other regions of the body open to allow expiratory airflow. Below the threshold expiration may be limited.

Figure 3:
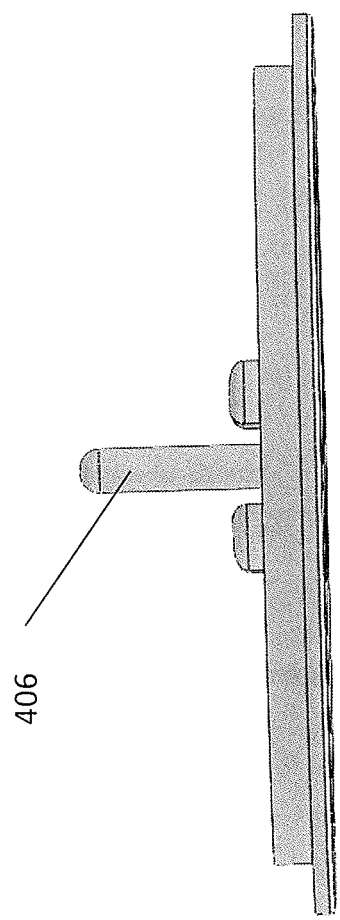
FIG. 3 shows a side view of the cap end region of a device similar to the variation shown in FIGS. 1A and 1B.
Figure 4:
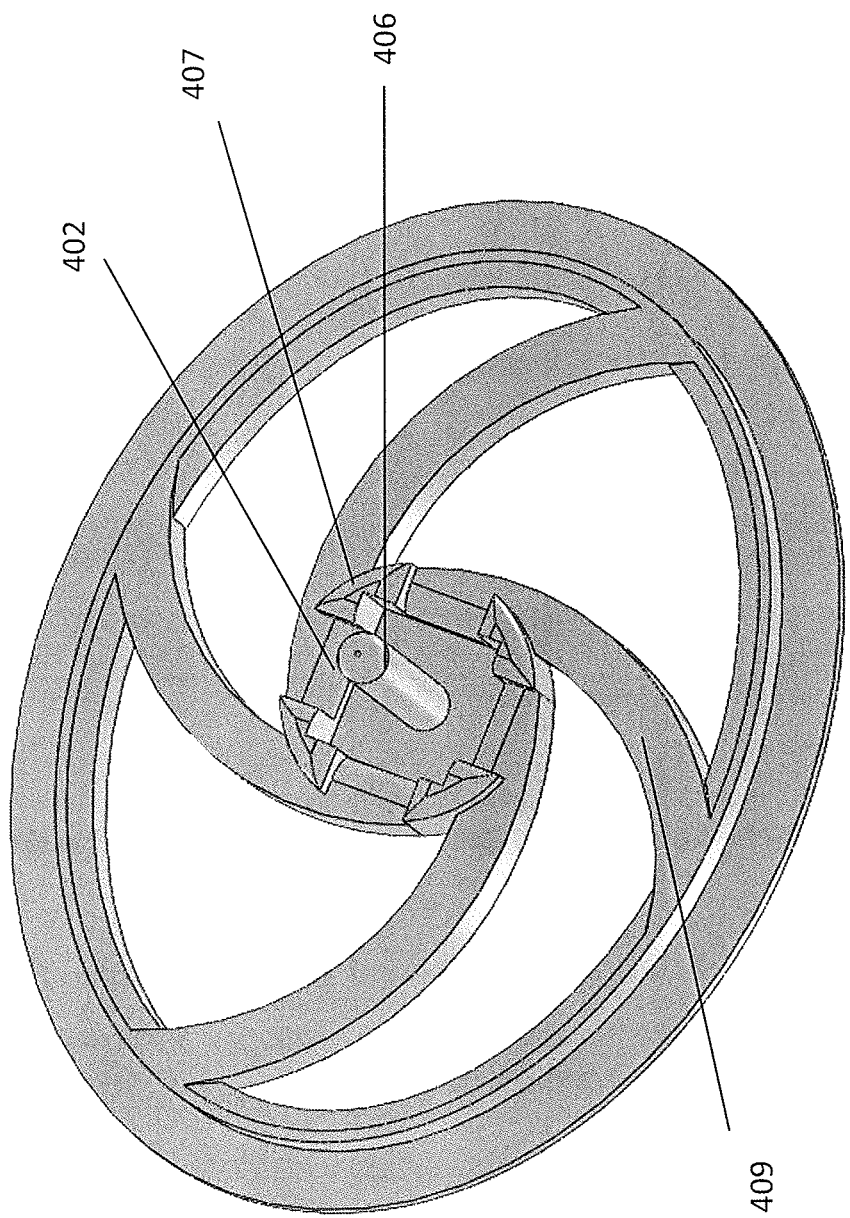
FIG. 4 shows a bottom perspective view of the cap end region of a device similar to the variation shown in FIGS. 1A and 1B.

Thus, in FIGS. 3 and 4, a cap portion is shown in side and side perspective views, respectively. The cap may mate with the body region (shown in FIGS. 8A-8B), over a piston region (shown in FIGS. 5-7). The cap may have a thickness, e.g. of around 1 mm (e.g., between 0.8 mm and 1.5 mm, e.g., 1.2 mm) which may provide a relatively stiff support. The cap may include rib notches 402 for mating with ribs (e.g. on the piston). The corners 407 forming the notches may act as bearing surfaces for displacement of the cap during operation (above the cracking threshold of expiratory pressure). A spring post 406 is included which may hold the spring within the assembly including the body and the cap region. The spiral shapes 409 may be configured so inhalation (inspiration) through the assembly may be only minimally impeded during operation. For example, the spiral shapes shown add only about 0.05 cm H2O to the inspiratory resistance at 300 mL/s flow. This may be contrasted with the somewhat larger resistance when using one or more straight crossbars. In operation, this cap member may be displaced to allow expiration through the device above the threshold expiratory pressure.

Figure 5:
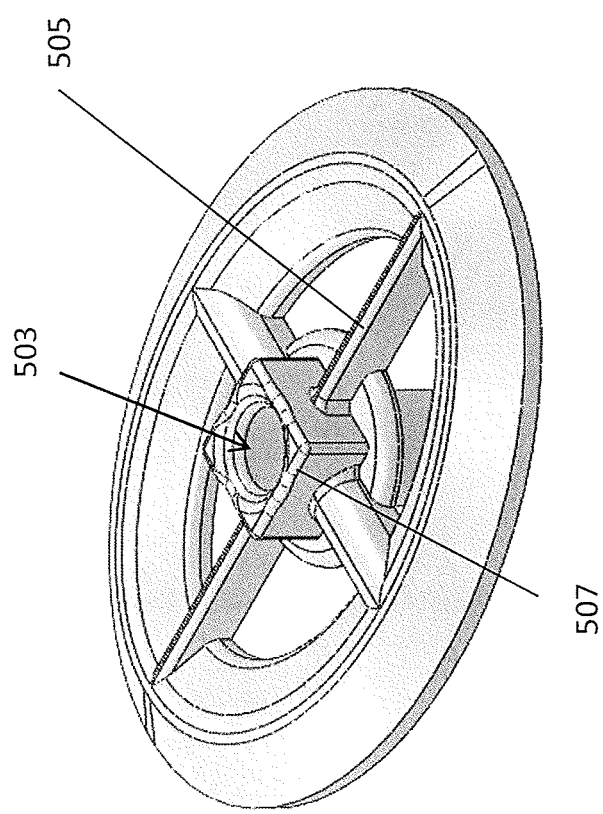
FIG. 5 shows a top perspective view of the piston region of a device similar the device shown in FIGS. 1A and 1B.
Figure 6:
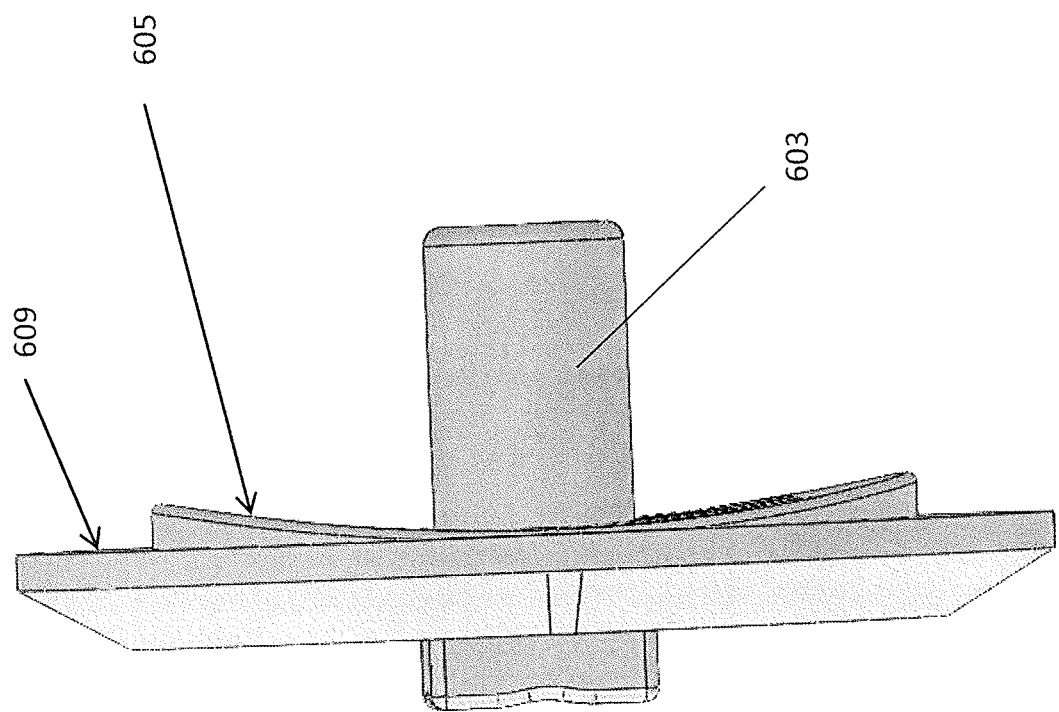
FIG. 6 shows a side view of the piston region of a device similar to that shown in FIGS. 1A and 1B.
Figure 7:
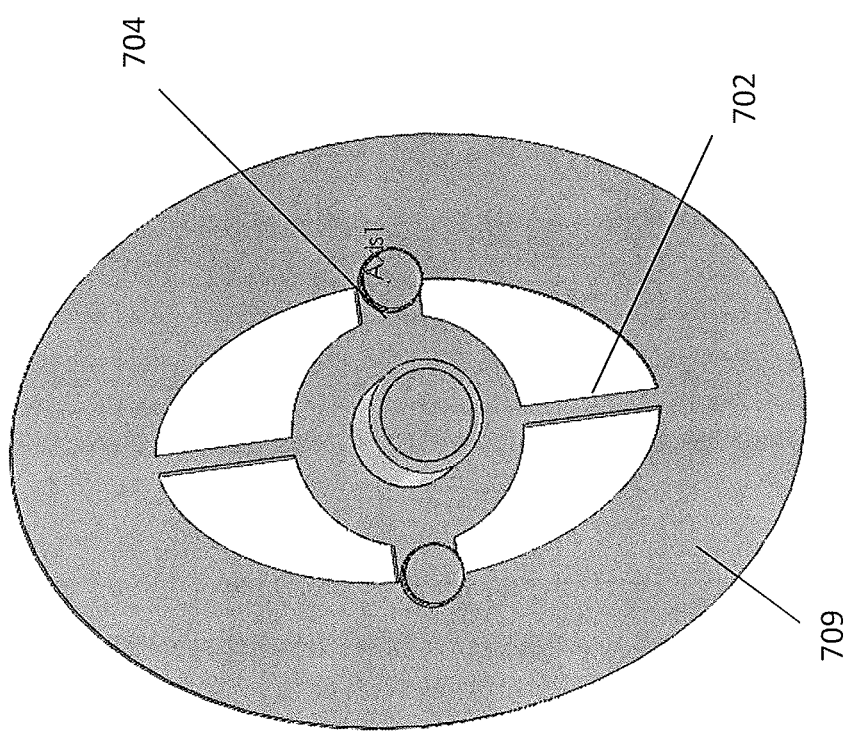
FIG. 7 shows a bottom perspective view of the piston region of a device similar the device shown in FIGS. 1A and 1B.

FIGS. 5-7 illustrate the piston member that may be held between the cap and the body. As illustrated in FIG. 5, the piston may include a spring hole 503, and surrounding male bearing surfaces 507 (which may mate with the cap bearing surfaces 407. The ribs 505 may extend from the spring hole and support the edge region, and may also faun a support for the internal flap valve (not shown). The flap valve may overlap enough so as not to blow through (e.g., by removed from) the device during exhalation; the surface of the piston may provide sufficient contact with the flap so that it can seal against the surface during exhalation, and there is sufficient clearance so that the flap valve can open upon inhalation.

For example, in FIG. 6, the piston includes a flap valve ("flapper") seat 605. This seat may be curved. Curving the seat may enhance the seal and may reduce undesirable vibration during operation. The piston may also include a piston valve seat region 609, and a spring cylinder (which may house a spring, not shown, providing the biasing force).

FIG. 7 shows a bottom view of the piston. As shown, two of the ribs 702 may be made as thin as possible (e.g. 0.4 or 0.5 mm), while the horizontal ribs 704 may be thicker; in some variations the flap valve may bend along the horizontal ribs. The surface 709 may form part of the piston valve seat.

Figure 8A:
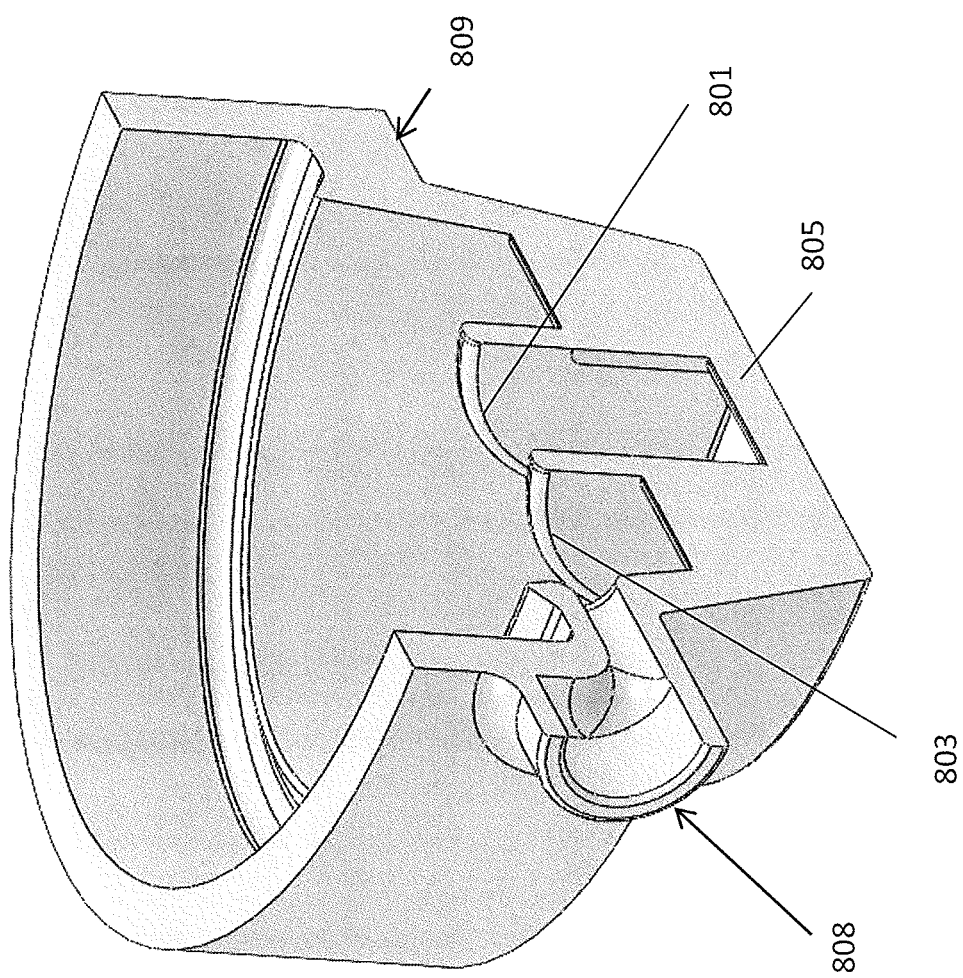
FIG. 8A shows a side perspective view of a cut-away section of a body region of a passive nasal PEEP device as illustrated in FIGS. 1A and 1B.

FIG. 8A shows a partially cut-away side view of the body portion of the assembly, which may form a passage to be placed in communication with a nostril. In this example, the body includes a cannula attachment region 808; the cannula may be used to sample the pressure within the device during operation (and/or the pressure within the nostril). The body may be connected to the adhesive holdfast (not shown), e.g., on a shelf around the body 809. The cone shape may include a journal region 805 to increase stiffness of the cone region. In FIG. 5, flap valve folding guides 801, 803 are also shown to help guide folding/bending of the internal flap valve.

Figure 8B:
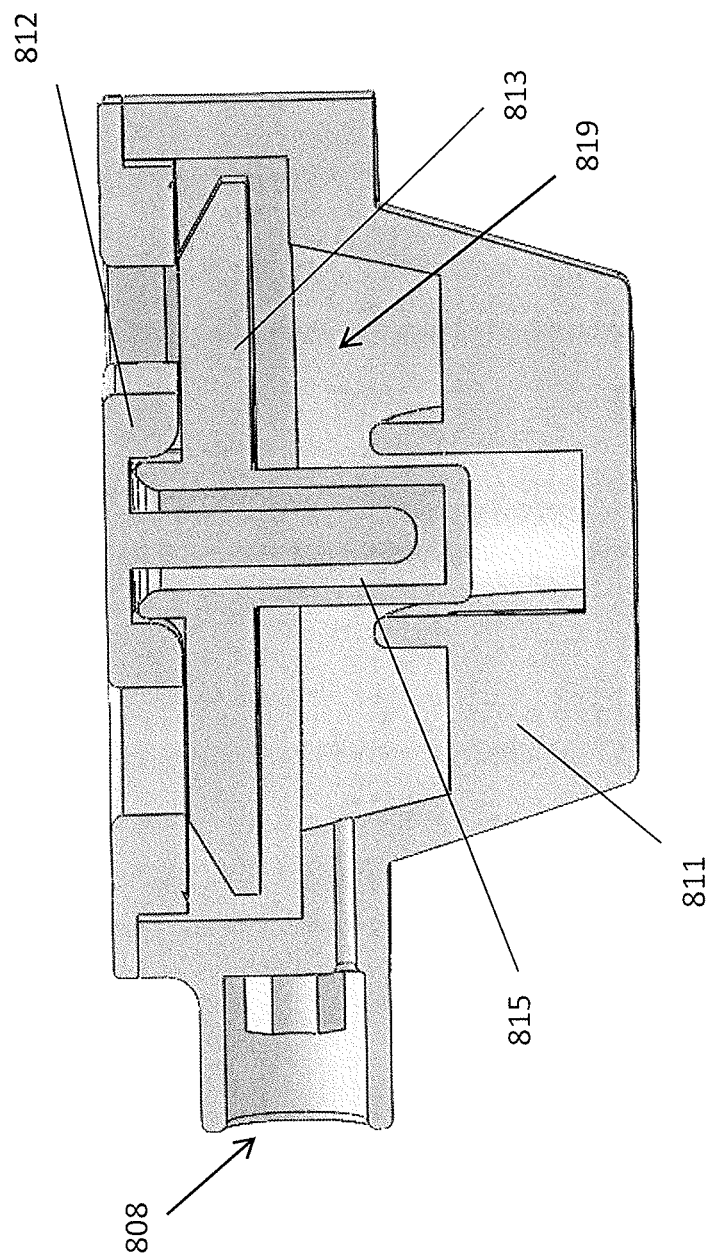
FIG. 8B is a section through the body region of the passive nasal PEEP device.

FIG. 8B shows a side cross-section through the assembly, including the body 811, the piston, 813, and the cap 812. A spring or other biasing member (not shown) may be positioned in the assembly in the biasing region 815. A flap valve (not shown) may also be positioned within the assembly 819 so that it can open during inhalation and close during exhalation.

Figure 9A:
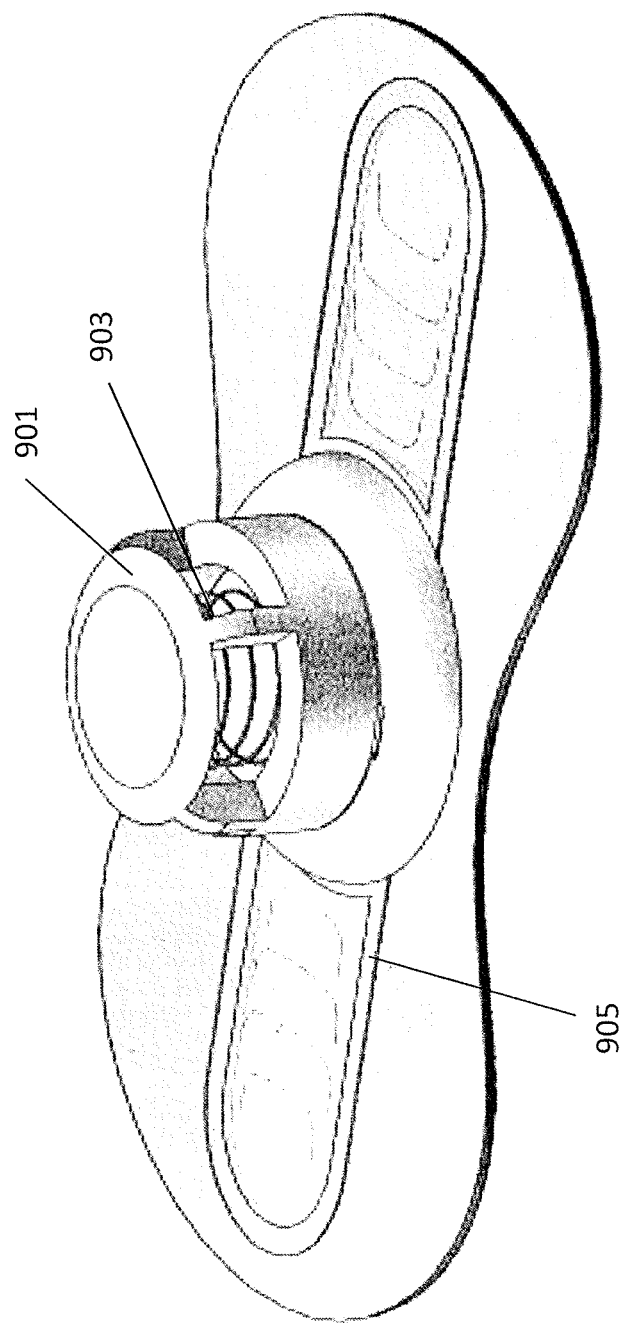
FIG. 9A shows a top perspective view of another variation of a passive nasal PEEP device configured to be placed over both of a subject's nostrils (a "whole nose" configuration).
Figure 9B:
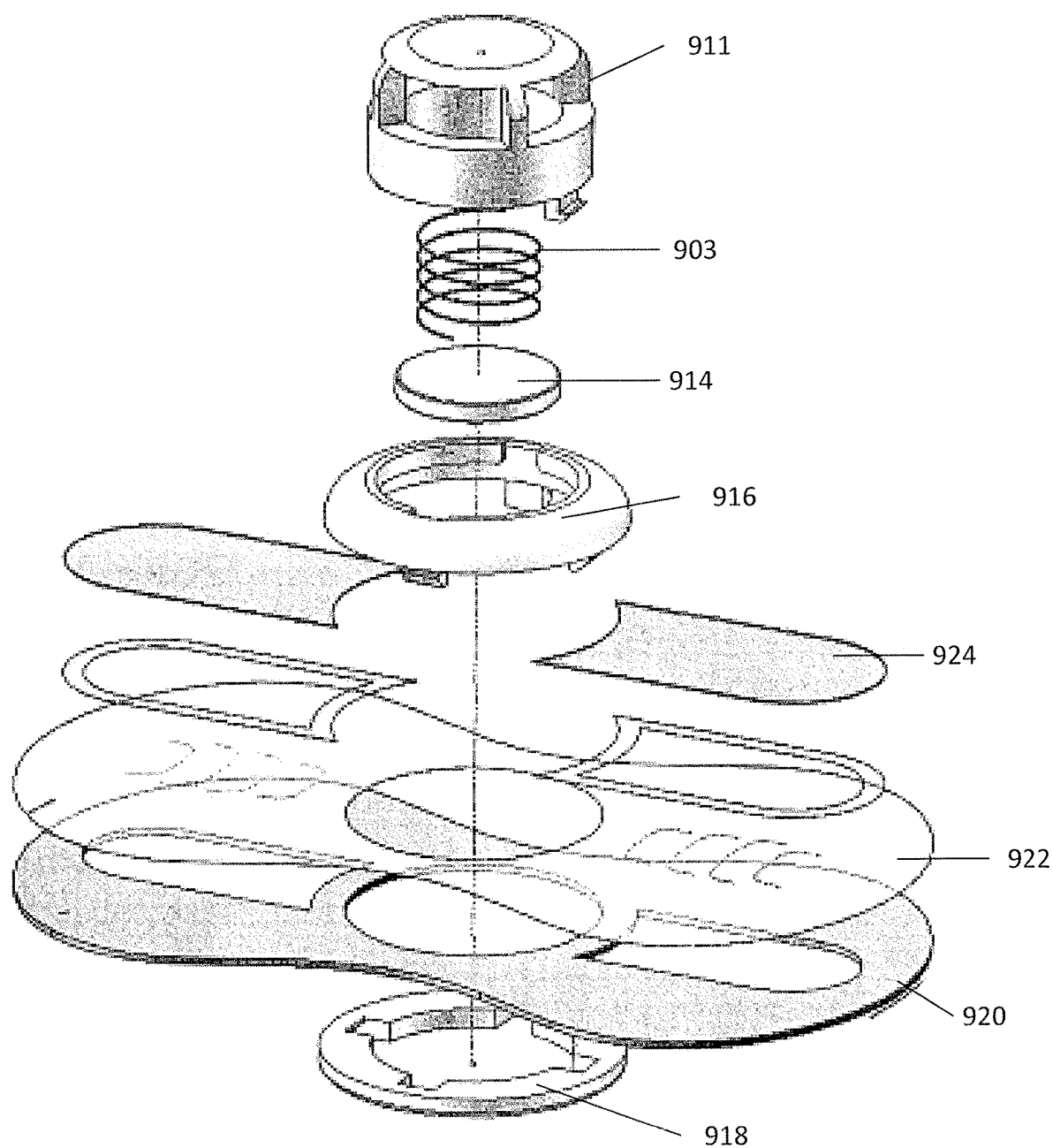
FIG. 9B shows an exploded view of the various components of the device shown in FIG. 9A.

Finally FIGS. 9A and 9B illustrate a whole-nostril variation. In FIGS. 9A ("closed" during exhalation at low pressure) and 9B (showing an exploded view), the device is adapted with a central "release" region that is biased to open during exhalation above the threshold. The release region includes a housing 901 with a bias (spring) 903. The housing may be reusable, e.g., by replacing the adhesive holdfast and flap regions 905.

In the exploded view of FIG. 9B, the housing includes a cover (polymeric region 911), a bias 903 (e.g., spring), a pressure plate 914, and an upper cover base 916 and a lower cover base 918. The whole-nose (e.g., both nostrils) apparatus may also include a holdfast 920 that includes an adhesive and may also include an adhesive backing (e.g., foam, etc.), a flap layer 922 (e.g., polyethylene) with one or more cut-out flaps, and a flap restricting layer or limiting layer 924 that prevents the flaps from opening during exhalation. The entire device may be configured so that exhalation pressure from either or both nostrils may be sufficient to open the release valve above a threshold pressure. In any of the whole-nose variations the nested valve (including the bias within the housing) may be centrally located between, or otherwise in communication with, both nostrils. In some variations multiple nested valves may be used, e.g., each positioned over a nostril region.

As mentioned above, in any of these variations the device may be used with a mask, rather than directly attaching to the nostril. For example, FIGS. 3 and 4 show components that may be used to form a cap region of some variations of the device. In some variations the device includes a cap region.

Threshold Pressure

In some embodiments, a pre-loaded spring (forming part of the expiratory valve of the airflow resistor) selectively restricts the opening of the expiratory valve. Expiratory flow is possible only when the pressure of the patient's airstream exceeds the cracking pressure of the valve. Selection of a spring that has a large preload distance relative to maximum valve displacement ensures that the expiratory pressure provided to the patient stays close to constant as airflow increases, instead of the pressure increasing significantly with increasing pressure. A ratio of preload distance to maximum valve displacement between 2:1 to 8:1 has been found to be effective for this purpose. The spring may be a compression spring, extension spring, or torsion spring. Other embodiments utilize magnets, rather than springs, to provide an expiratory threshold valve.

Inspiratory Resistance

In some embodiments, the inspiratory and expiratory valves are nested, rather than acting in parallel. Nesting both the inspiratory and expiratory valves increases the cross-sectional area available to each valve. (If the valves are acting in parallel, an increase in the cross-section area occupied by one valve reduces the area available for the other valve). Increasing the cross-sectional areas for the inspiratory valve is important because higher cross-sectional area enables lower inspiratory resistance. Minimizing inspiratory resistance of the inspiratory valve is important, as this can be the major contributor to inspiratory resistance of the entire device. Minimizing inspiratory resistance of the device is critical, as this minimizes the pressure drop across the device during inspiration, thereby causing a sleep apnea patient's airway pressure to be less negative, and therefore less likely to collapse. Also, increasing the cross-sectional area available for the expiratory valve is important because it increases the force of spring that can be used to achieve a given threshold pressure. This enables use of a stiffer, easier to manufacture spring.

Moisture frequently condenses on the inner surfaces of PEEP valve devices. This moisture can be present between the inspiratory valve flapper and the valve seat of the piston, and it can increase the pressure required to open the inspiratory valve. In some embodiments, the side of the flapper facing the valve seat of the piston, and the valve seat of the flapper, have a hydrophobic surface. These hydrophobic surfaces may be attained by high surface roughness, by a low surface energy coating, or other means.

Device Thickness

Minimizing the distance that the device protrudes out of the nostrils may be important for several reasons: minimizing the visual presence of the device, in order to make it less obtrusive and more acceptable for users; reducing the likelihood that the device will rub against other objects such as a pillow during sleep; and reduce the likelihood that the device would contact a male patient's facial hair.

In some embodiments, the housing for the compression spring in the piston extends beyond the plane of the valve seat, and protrudes into the nose cone of the body. Positioning the spring in this way, instead of placing the spring so its full length extended above the piston's valve seat, and did not protrude into the nose cone of the body, enables the overall device height to be reduced.

In some embodiments, the piston, body, and endcap components are made from a high stiffness plastic. High stiffness plastics that could be selected for these parts include Vectra liquid crystal polymer, polyether ether ketone, carbon filled nylon, and glass filled nylon. In other embodiments, the piston, body, and endcap components are made from a metal. Aluminum or stainless steel alloys could be selected for these parts.

Seal at Low Expiratory Flow

To maintain positive pressure in the airway, during end-expiratory pause, it is desirable for the device to maintain a therapeutic level of pressure at low expiratory flow rates.

In some embodiments, the inspiratory valve flapper is an elastomer. A highly compliant elastomer that is capable of significant strain before plastic deformation occurs, is well suited for this application. Such a material helps insure that the inspiratory valve flapper will not be deformed (for example, during assembly), which could cause a leak path between the flapper and the valve seat of the piston, and thus prevent adequate pressure from being maintained at low expiratory flow rates.

In some embodiments, the inspiratory valve flapper is adhered to the piston with an adhesive that has a negligible or low shrinkage rate. Shrinkage of the adhesive for this joint could distort the surface of the flapper and cause leakage paths. In other embodiments, the inspiratory valve flapper is retained from translating during inspiration by a retaining feature or part. In these embodiments, no adhesive contacts the inspiratory valve flapper.

In some embodiments, the inspiratory valve flapper has an interference fit with the piston's spring cylinder. This overlap may impart residual stresses in the flapper that bias it to a closed position. In other embodiments, the inspiratory valve flapper does not have an interference fit with any other parts. The lack of interference fit may reduce distortions to the flapper and reduce leak paths at low flow.

In some embodiments, the piston's valve seat is not flat. In some embodiments, the valve seat has an arc along the major axis. In this embodiment, the curvature of the piston's valve seat prevents a leak path from being exposed when the ends of inspiratory valve flapper bend due to gravity. In other embodiments, the valve seat has an arc along the minor axis. This curvature reduces the magnitude of bending of the inspiratory valve flapper along the major axis due to gravity, thus reducing the potential leak path.

Nasal Cannula Attachment

It is desirable for the nasal PEEP valve device to be able to integrate with a nasal cannula, in order to facilitate monitoring of nasal pressure during a sleep study.

The nasal cannula compatible embodiment of the body contains a housing for connecting to nasal cannula tubing, and a passageway with fluid communication between the housing and the inner surface of the nose cone, which is in constant fluid communication with the patients nasal passage when the device is in use. This enables the measurement of intranasal pressure. Measurement of intranasal pressure provides accurate data on the pressure delivered to the patient during expiration, whereas other potential measurement systems may not output the actual pressure delivered to the patient. Additionally this system provides accurate data on the pressure drop across the device during inspiration which may be helpful for healthcare practitioner to monitor.

In some embodiments, the tubing housing of the nasal cannula compatible body and the passageway to the inner surface of the nose cone are not concentric. This avoids adding unnecessary height to the body's valve seat, thus enabling the overall height of the device to be minimized.

It is important for the facial adhesive to be easy to apply for the patient. Even with nasal cannula tubing extending from the nasal PEEP valve device, it must be easy to achieve a good seal with the facial adhesive. In order to accomplish this, in some embodiments the housing for the nasal cannula tubing is angled between the major and minor axes of the device. In other embodiments, the housing for the nasal cannula tubing is angled towards the endcap (and away from the nose cone), in order to provide the patient with more space in which to apply the facial adhesive.

Noise

It is important for the device to make as little noise as possible during use, in order to avoid disturbing the patient and their bed partner.

The flapper alignment guides in the nose cone of the body restrict the bending of the inspiratory valve flapper during inspiration. The presence of these guides greatly reduces vibration and noise during inspiration.

Nose Cone Stiffness

During use, the nose cone of the body sits in the patient's nostrils. It is desirable for the nose cone to have as thin walls as possible, in order to maximize the cross-sectional area of the nose cone. On the other hand, it is desirable for the nose cone to be stiff and for it to be resistant to plastic deformation. To address this, in some embodiments of the nose cone there is a beam across the minor axis connecting the two sides of the cone. This provides a stiff, deformation-resistant cone with thin walls.

Stiction Between Piston and Body

Moisture frequently condenses on the surface of the piston's valve seat and the body's valve seat. It is possible for such condensation to cause stiction at the beginning of expiration, which causes the patient for experience a "popping" sensation. It is desirable to minimize or eliminate this effect.

In some embodiments, the contact surface area of the body's valve seat is minimized. In some embodiments, the contact surface is a rim with a sharp angle, approximating a line contact. In other embodiments, the contact surface is a series of small nubs that protrude above the surface of the rest of the body's valve seat.

In some embodiments, piston's valve seat and the body's valve seat are constructed to be hydrophobic. This results in less water adhering to the surfaces, as well as weaker water-solid interactions. Two methods that may be used to make these surfaces hydrophobic are application of a rough surface finish and application of a low surface energy coating.

In some embodiments, a compliant element allows one side of the piston's valve seat to open before the other, reducing the stiction force that must be overcome at a given instant in time.

Binding in Bearing

In some iterations of the device, binding in the bearing between the piston and the endcap caused an uneven exhalation with the sensation of "popping"

In some embodiments, a circular bearing is used (rather than a square bearing, for example), to reduce the chance of bearing binding due to rotation.

In some embodiments, the male bearing surface of the piston and female bearing surface of the endcap are constructed to have a low coefficient of friction.

In some embodiments, the male bearing surface of the piston is tapered, providing greater play when less of the bearing surface is engaged.

In some embodiments, there is a large pathway providing fluid communication between the outside of the device and the inner wall of the body, providing expiratory flow a pathway to directly exit the device after passing through the expiratory valve. This may reduce the proportion of the moist expiratory airflow that passes over the bearing, and thereby reduce the water deposited on the bearing.

Combination Therapy

In some methods of treatment of sleep disordered breathing patients with nasal PEEP valves, a means to restrain the patients mouth in a closed position, such as a chin strap, is used in conjunction.

Patient Selection

In some methods of treatment of sleep disordered breathing patients with nasal PEEP valves, patients are selected for this therapy based on nasal resistance screening or upper airway resistance screening.

Oral-Nasal Therapy

In some embodiments and methods, a threshold valve through which inspiration is less restricted than expiration, is applied to either the nose or mouth, and the other is sealed to prevent air leaks.

In other embodiments, a threshold valve through which inspiration is less restricted than expiration, is applied to both the nose and mouth.

Auto-Titrating PEEP Valve

In some embodiments and methods, a threshold valve for treating sleep disordered breathing comprises: a sensor, an actuator, an adjustable expiratory valve, and an inspiratory valve. In these embodiments and methods, the threshold valve would continually adjust the expiratory pressure delivered to the patient, based on the information received by the sensor related to the efficacy of the treatment. Among the advantages of an auto-titrating PEEP valve are:

The ability for a patient to have customized therapy delivered to treat their sleep disordered breathing. The ability for a patient to receive varying levels of pressure over the course of a night. At any time, the patient would receive no more pressure than necessary, thereby minimizing discomfort.

Additionally, some embodiments and methods of the auto-titrating PEEP valve have a ramp function, whereby pressure is reduced while the patient is attempting to fall asleep, and subsequently increased once the patient is asleep. In some embodiments, a timer is used to support the implementation of this ability. In other embodiments, a sensor to detect whether the patient is sleeping is used.

Diagnostic Devices

It may also be desirable to titrate the appropriate pressure to use in treating sleep disordered breathing using a threshold valve.

In some embodiments and methods, a threshold valve can be adjusted to provide multiple pressure settings.

In some embodiments and methods, the pressure settings are adjusted manually, by moving part of the device while it is attached to the patient. For example, a sleep technician can rotate a knob on the device, thereby changing the preload of a spring, and adjusting the expiratory threshold pressure. In other embodiments and methods, the pressure settings can be adjusted without physically touching the device, thereby avoiding waking the patient up. For example, the sleep technician can select a pressure from a digital interface, and this pressure is communicated to the device via wires or wirelessly. The device contains a microcontroller and adjusts the expiratory threshold pressure in accordance to the new input signal.

In some embodiments and methods, the pressure settings are discrete. In others, pressure settings cover a continuous range.

In some embodiments and methods, a respiratory support device that provides active pressure delivers expiratory positive airway pressure (EPAP) to a patient, in order to titrate the pressure needed for a threshold expiratory valve to treat sleep disordered breathing.

In some embodiments and methods, an auto-titrating threshold valve is used for titration of sleep disordered breathing patients.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A nasal respiratory device for inducing positive end-expiratory pressure that is configured to be worn in communication with a subject's nose, the device comprising:
   a body region having an opening;
   a first passive airflow resistor in communication with the opening, wherein the first passive airflow resistor is configured to open during inhalation, and substantially close during exhalation;
   a second passive airflow resistor that is configured to open during exhalation from a closed position when expiratory pressure is greater than a non-zero threshold pressure, so that the second passive airflow resistor opens when the expiratory pressure across the second airflow resistor exceeds the threshold pressure for opening during expiration; and
   a holdfast configured to adhesively secure the device over, across or within one or both of a subject's nostrils without covering the subject's mouth.

2. The device of claim 1, wherein the first passive airflow resistor is a flap valve.

3. The device of claim 1, wherein the first passive airflow resistor is a plurality of flap valves.

4. The device of claim 1, wherein the second passive airflow resistor is nested relative to the first passive airflow resistor.

5. The device of claim 1, wherein the second passive airflow resistor includes a biasing element preventing opening below the threshold pressure.

6. The device of claim 5, wherein the biasing element is a spring.

7. The device of claim 1, wherein the holdfast is configured to secure the device over both of the subjects nostrils.

8. The device of claim 1, wherein the opening is formed through a housing.

9. The device of claim 8, wherein the housing houses the first passive airflow resistor and the second passive airflow resistor.

10. The device of claim 1, wherein the second passive airflow resistor comprises a piston member configured to be displaced when the expiratory pressure is above the threshold pressure.

11. The device of claim 1, wherein the threshold pressure is between about 1 cm $H_2O$ and about 20 cm $H_2O$.

12. The device of claim 1, further comprising a nasal airflow monitor to measure nasal airflow.

13. The device of claim 12, wherein the nasal airflow monitor comprises a cannula attachment configured to couple to a nasal cannula.

14. The device of claim 1, wherein the holdfast includes a compliant material with an adhesive.

15. The device of claim 1, wherein the holdfast is configured to secure at least a portion of the body within the one or both of the subject's nostrils.

16. The device of claim 1, wherein the holdfast is configured to secure at least a portion of the body outside of the one or both of the subject's nostrils.

17. A nasal respiratory device for inducing positive end-expiratory pressure that is configured to be worn in communication with a subject's nose, the device comprising:
- a housing forming an opening and having a body region;
- a first airflow resistor within the housing and configured to open during inhalation through the opening and close during exhalation through the opening;
- a second airflow resistor within the housing wherein the second airflow resistor is configured to have a non-zero threshold pressure for opening from a closed position during expiration through the opening, so that the second airflow resistor opens when a pressure across the second airflow resistor exceeds the threshold pressure for opening during expiration; and
- an adhesive holdfast extending from the housing and configured to secure the device over, across or within one or both of a subject's nostrils without covering the subject's mouth.

* * * * *